United States Patent [19]

Holmwood et al.

[11] Patent Number: 4,904,298
[45] Date of Patent: Feb. 27, 1990

[54] 1-HYDROXYETHYL-AZOLE COMPOUNDS AND AGRICULTURAL COMPOSITIONS

[75] Inventors: Graham Holmwood, Wuppertal; Karl H. Büchel, Burscheid; Klaus Lürssen, Berg-Gladbach; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 58,479

[22] Filed: Jun. 5, 1987

Related U.S. Application Data

[60] Division of Ser. No. 621,968, Jun. 18, 1984, Pat. No. 4,723,984, which is a division of Ser. No. 549,867, Nov. 8, 1983, which is a continuation of Ser. No. 260,479, May 4, 1981, abandoned.

[30] Foreign Application Priority Data

May 16, 1980 [DE] Fed. Rep. of Germany ....... 3018866
Feb. 19, 1981 [DE] Fed. Rep. of Germany ....... 3106076

[51] Int. Cl.$^4$ .................. A01N 43/653; C07D 249/08
[52] U.S. Cl. ........................................... 71/92; 71/76; 514/184; 514/383; 548/262; 548/101
[58] Field of Search ................ 548/101, 262; 514/184, 514/383; 71/92, 76

[56] References Cited

U.S. PATENT DOCUMENTS

| | | | |
|---|---|---|---|
| 4,005,083 | 1/1977 | Buchel et al. | 548/262 |
| 4,414,210 | 11/1983 | Miller et al. | 548/262 |
| 4,551,469 | 11/1985 | Parry et al. | 514/383 |
| 4,772,623 | 9/1988 | Timmler et al. | 548/262 |

Primary Examiner—Glennon H. Hollrah
Assistant Examiner—Patricia L. Morris
Attorney, Agent, or Firm—Sprung Horn Kramer & Woods

[57] ABSTRACT

New 1-hydroxyethyl-azole derivatives of the general formula

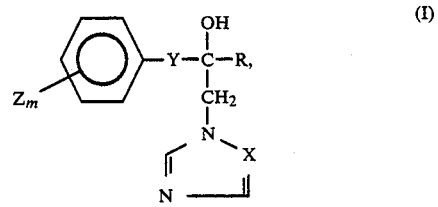

in which
R represents an alkyl radical, an optionally substituted cycloalkyl radical or an optionally substituted phenyl radical,
X represents a nitrogen atom or a CH group,
Y represents a grouping —OCH$_2$—, —CH$_2$CH$_2$— or —CH=CH—,
Z represents a halogen atom, an alkyl, cycloalkyl, alkoxy, alkylthio, halogenoalkyl, halogenoalkoxy or halogenoalkylthio radical, an optionally substituted phenyl radical, an optionally substituted phenoxy radical, an optionally substituted phenylalkyl radical or an optionally substituted phenylalkoxy radical and
m is 0, 1, 2 or 3, a process for their preparation and their use as plant growth regulators and fungicides.

8 Claims, No Drawings

1-HYDROXYETHYL-AZOLE COMPOUNDS AND AGRICULTURAL COMPOSITIONS

This is a division of application Ser. No. 621,968, filed June 18, 1984, now U.S. Pat. No. 4,723,984, which in turn is a division of Ser. No. 549,867, filed Nov. 8, 1983, now pending, which in turn is a continuation of Ser. No. 260,479, filed May 4, 1981, now abandoned.

This invention relates to certain new 1-hydroxyethyl-azole compounds. In additional aspect, the invention relates to plant growth regulant and fungicidal compositions containing such compounds and to methods of regulating plant growth and of combatting fungi utilizing such compounds.

It is known that certain 2-haloethyl-trialkyl-ammonium halides have plant growth regulating properties (see U.S. Pat. No. 3,156,554). Thus, for example, an influence on plant growth, in particular an inhibition of the vegetative plant growth of important crop plants, can be achieved with the aid of 2-chloroethyl-trimethyl-ammonium chloride. However, the activity of this substance is not always satisfactory, above all when low amount are applied.

It is also known that 2-chloroethylphosphonic acid has a plant growth-regulating action (see DE-OS (German Published Specification) 1,667,968). However, the results achieved with this substance are likewise not always satisfactory.

It has also ready been disclosed that zinc ethylene-1,2-bisdithiocarbamidate is a good agent for combating fungal plant diseases (see Phytopathology 33, 1113 (1963)). However, it can be used only to a limited extent, since its action is not always satisfactory, especially when low amounts and concentrations are applied.

The present invention now provides, as new compounds the 1-hydroxyethyl-azole derivatives of the general formula

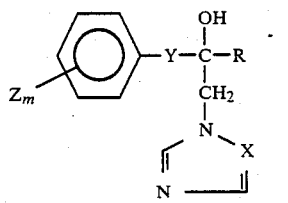

in which
R represents an alkyl radical, an optionally substituted cycloalkyl radical or an optionally substituted phenyl radical,
X represents a nitrogen atom or a CH group,
Y represents a grouping —OCH$_2$—, —CH$_2$CH$_2$— or —CH=CH—,
Z represents a halogen atom, an alkyl, cycloalkyl, alkoxy, alkylthio, halogenoalkyl, halogenoalkoxy or halogenoalkylthio radical, an optionally substituted phenyl radical, an optionally substituted phenoxy radical, an optionally substituted phenylalkyl radical or an optionally substituted phenylalkoxy radical and
m is 0, 1, 2 or 3.
and acid addition salts and metal salt complexes thereof.

The compounds of the formula (I) have an asymmetric carbon atom and can therefore be obtained in the two optical isomer forms. If Y represents the grouping —CH=CH—, the compounds of the formula (I) can additionally exist in two geometric isomer forms. The present invention relates both to the isomer mixtures and to the individual isomers.

According to the present invention there is further provided a process for the production of a compound of the present invention, characterised in that an oxirane of the general formula

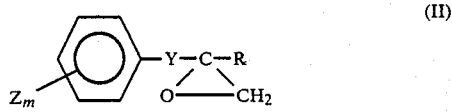

in which
R, Y, Z and m have the abovementioned meaning, is reacted with an azole of the general formula

in which
X has the abovementioned meaning,
in the presence of a diluent and if appropriate in the presence of a base, and the resulting compound of the formula (I) is then converted, if desired, into an acid addition salt or metal salt complex thereof.

It has also been found that the new 1-hydroxyethyl-azole derivatives of the present invention have powerful plant growth-regulating and powerful fungicidal properties.

Surprisingly, the 1-hydroxy-azole derivatives of the present invention exhibit a better plant growth-regulating action than 2-chloro-ethyl-trimethylammonium chloride, which is known, and 2-chloroethylphosphonic acid, which is likewise known, these compounds being recognised as highly active substances with the same type of action. The compounds according to the invention also have, surprisingly, a better fungicidal action than zinc ethylene-1,2-bisdithiocarbamidate, which is known from the state of the art and is a closely related compound from the point of view of its action. The active compounds according to the invention thus represent an enrichment of the art.

Preferred 1-hydroxyethyl-azole derivatives according to the present invention are those in which R represents a straight-chain or branched alkyl radical with 1 to 4 carbon atoms, a cycloalkyl radical which has 3 to 7 carbon atoms and is optionally substituted by alkyl with 1 to 2 carbon atoms, or a phenyl radical which is optionally monosubstituted or polysubstituted by identical or different substituents, preferred substituents being: halogen, alkyl with 1 to 4 carbon atoms and halogenoalkyl with 1 to 2 carbon atoms and 1 to 5 identical or different halogen atoms (such as, in particular, fluorine and chlorine atoms), Z represents a halogen atom, a straight-chain or branched alkyl radical with 1 to 4 carbon atoms, a cycloalkyl radical with 5 to 7 carbon atoms, an alkoxy or alkylthio radical with in each case 1 to 4 carbon atoms, a halogenoalkyl, halogenoalkoxy or halogenoalkylthio radical with in each case 1 or 2 carbon atoms and 1 to 5 identical or different halogen atoms (such as, in particular, fluorine and chlorine atoms), or a phenyl, phenoxy, phenylalkyl or phenylalkoxy radical, in each case optionally substituted, the phenylalkyl and phenylalkoxy radicals having 1 to 2 carbon atoms in the alkyl part or in the alkoxy part, and preferred substituents which may be mentioned being: halogen and alkyl with 1 to 4 carbon atoms, and X, Y and m have the meanings indicated above.

Particularly preferred compounds of the formula (I) are those in which R represents a tert.-butyl, isopropyl or methyl radical, or a cyclopropyl, cyclopentyl or cyclohexyl radical, in each case optionally substituted by methyl, or phenyl which is optionally monosubstituted or disubstituted by identical or different substituents selected from fluorine, chlorine, methyl and trifluoromethyl, Z represents a fluorine, chlorine or bromine atom, a methyl, tert.-butyl, cyclohexyl, methoxy, methylthio, trifluoromethyl, trifluoromethoxy or trifluoromethylthio radical, or a phenyl, phenoxy, benzyl or benzyloxy radical, in each case optionally monosubstituted or disubstituted by identical or different substituents selected from fluorine, chlorine and methyl, and X, Y and m have the meaning indicated above.

The following compounds of the general formula (I) may be mentioned specifically, in addition to the compounds mentioned in the Preparative Examples:

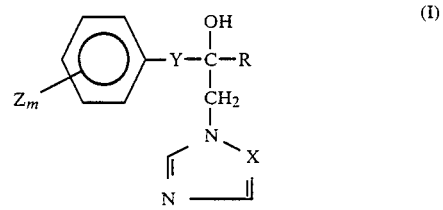

(I)

TABLE 1

| $Z_m$ | Y | R | X |
|---|---|---|---|
| 4-C₆H₅ | —O—CH₂— | —C(CH₃)₃ | N(CH) |
| 4-(4-Cl-C₆H₄) | " | " | " |
| 4-O-C₆H₅ | " | " | " |
| 4-O-(4-Cl-C₆H₄) | " | " | " |
| 4-CH₂-C₆H₅ | " | " | " |
| 4-CH₂-(4-Cl-C₆H₄) | " | " | " |
| 4-O-CH₂-C₆H₅ | " | " | " |
| 4-O-CH₂-(4-Cl-C₆H₄) | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |

TABLE 1-continued

| $Z_m$ | Y | R | X |
|---|---|---|---|
| 4-C₆H₅ | —O—CH₂ | 4-Cl-C₆H₄ | N(CH) |
| 4-(4-Cl-C₆H₄) | " | " | " |
| 4-O-C₆H₅ | " | " | " |
| 4-O-(4-Cl-C₆H₄) | " | " | " |
| 4-CH₂-C₆H₅ | " | " | " |
| 4-CH₂-(4-Cl-C₆H₄) | " | " | " |
| 4-O-CH₂-C₆H₅ | " | " | " |
| 4-O-CH₂-(4-Cl-C₆H₄) | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 4-C₆H₅ | —O—CH₂— | —CH(CH₃)₂ | N(CH) |
| 4-(4-Cl-C₆H₄) | " | " | " |
| 4-O-C₆H₅ | " | " | " |
| 4-O-(4-Cl-C₆H₄) | " | " | " |

TABLE 1-continued

| $Z_m$ | Y | R | X |
|---|---|---|---|
| 4-CH<sub>2</sub>–C<sub>6</sub>H<sub>5</sub> | " | " | " |
| 4-CH<sub>2</sub>–C<sub>6</sub>H<sub>4</sub>–Cl | " | " | " |
| 4-O–CH<sub>2</sub>–C<sub>6</sub>H<sub>5</sub> | " | " | " |
| 4-O–CH<sub>2</sub>–C<sub>6</sub>H<sub>4</sub>–Cl | " | " | " |
| 3,4-Cl<sub>2</sub> | " | " | " |
| 4-CF<sub>3</sub> | " | " | " |
| 4-OCF<sub>3</sub> | " | " | " |
| 4-SCF<sub>3</sub> | " | " | " |
| 4-SCH<sub>3</sub> | " | " | " |
| 4-C(CH<sub>3</sub>)<sub>3</sub> | " | " | " |
| 4-C<sub>6</sub>H<sub>5</sub> | —O—CH<sub>2</sub>— | H (cyclohexyl) | N(CH) |
| 4-C<sub>6</sub>H<sub>4</sub>–Cl | " | " | " |
| 4-O–C<sub>6</sub>H<sub>5</sub> | " | " | " |
| 4-O–C<sub>6</sub>H<sub>4</sub>–Cl | " | " | " |
| 4-CH<sub>2</sub>–C<sub>6</sub>H<sub>5</sub> | " | " | " |
| 4-CH<sub>2</sub>–C<sub>6</sub>H<sub>4</sub>–Cl | " | " | " |
| 4-O–CH<sub>2</sub>–C<sub>6</sub>H<sub>5</sub> | " | " | " |
| 4-O–CH<sub>2</sub>–C<sub>6</sub>H<sub>4</sub>–Cl | " | " | " |
| 3,4-Cl<sub>2</sub> | " | " | " |
| 4-CF<sub>3</sub> | " | " | " |

TABLE 1-continued
| $Z_m$ | Y | R | X |
|---|---|---|---|
| 4-OCF$_3$ | " | " | " |
| 4-SCF$_3$ | " | " | " |
| 4-SCH$_3$ | " | " | " |
| 4-C(CH$_3$)$_3$ | " | " | " |
| 4- 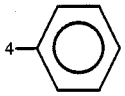 | —O—CH$_2$— |  | N(CH) |
| 4- 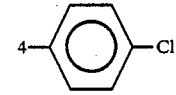 —Cl | " | " | " |
| 4-O— 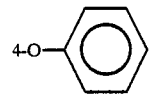 | " | " | " |
| 4-O— 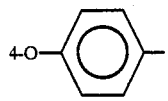 —Cl | " | " | " |
| 4-CH$_2$— 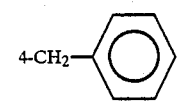 | " | " | " |
| 4-CH$_2$— 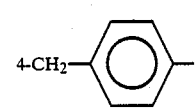 —Cl | " | " | " |
| 4-O—CH$_2$— 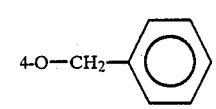 | " | " | " |
| 4-O—CH$_2$— 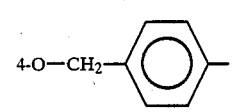 —Cl | " | " | " |
| 3,4-Cl$_2$ | " | " | " |
| 4-CF$_3$ | " | " | " |
| 4-OCF$_3$ | " | " | " |
| 4-SCF$_3$ | " | " | " |
| 4-SCH$_3$ | " | " | " |
| 4-C(CH$_3$)$_3$ | " | " | " |
| 4- 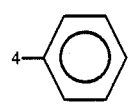 | —CH$_2$—CH$_2$— | —C(CH$_3$)$_3$ | N(CH) |
| 4- 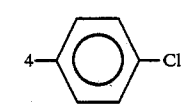 —Cl | " | " | " |
| 4-O— 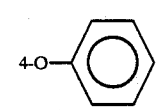 | " | " | " |

TABLE 1-continued
| $Z_m$ | Y | R | X |
|---|---|---|---|
| 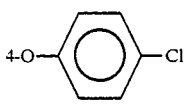 | " | " | " |
| 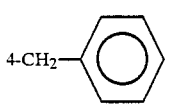 | " | " | " |
| 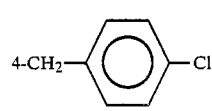 | " | " | " |
| 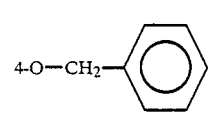 | " | " | " |
| 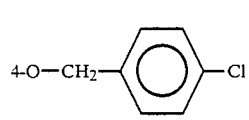 | " | " | " |
| 3,4-Cl$_2$ | " | " | " |
| 4-CF$_3$ | " | " | " |
| 4-OCF$_3$ | " | " | " |
| 4-SCF$_3$ | " | " | " |
| 4-SCH$_3$ | " | " | " |
| 4-C(CH$_3$)$_3$ | " | " | " |
| 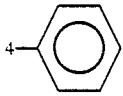 | —CH$_2$—CH$_2$— | 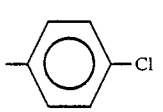 | N(CH) |
| 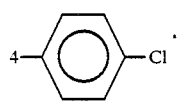 | " | " | " |
| 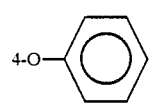 | " | " | " |
| 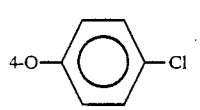 | " | " | " |
| 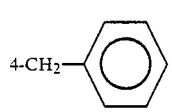 | " | " | " |
| 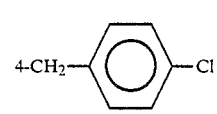 | " | " | " |
| 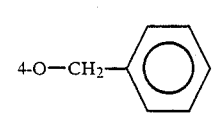 | " | " | " |

TABLE 1-continued
| $Z_m$ | Y | R | X |
|---|---|---|---|
| | " | " | " |
| 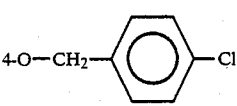 4-O—CH₂—⟨⟩—Cl | | | |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 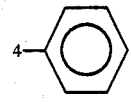 4-⟨⟩ | —CH₂—CH₂— | —CH(CH₃)₂ | N(CH) |
| 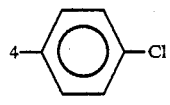 4-⟨⟩—Cl | " | " | " |
| 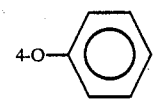 4-O-⟨⟩ | " | " | " |
| 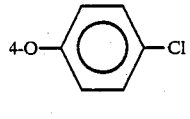 4-O—⟨⟩—Cl | " | " | " |
| 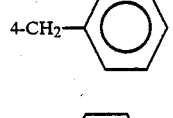 4-CH₂—⟨⟩ | " | " | " |
| 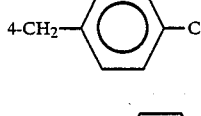 4-CH₂—⟨⟩—Cl | " | " | " |
| 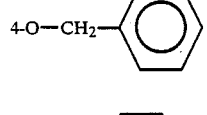 4-O—CH₂—⟨⟩ | " | " | " |
| 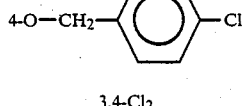 4-O—CH₂—⟨⟩—Cl | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 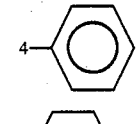 4-⟨⟩ | —CH₂—CH₂— | 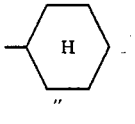 ⟨⟩—H | N(CH) |
| 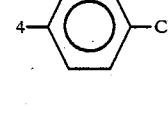 4-⟨⟩—Cl | " | " | " |

TABLE 1-continued

| $Z_m$ | Y | R | X |
|---|---|---|---|
| 4-O-C₆H₅ | " | " | " |
| 4-O-C₆H₄-Cl | " | " | " |
| 4-CH₂-C₆H₅ | " | " | " |
| 4-CH₂-C₆H₄-Cl | " | " | " |
| 4-O-CH₂-C₆H₅ | " | " | " |
| 4-O-CH₂-C₆H₄-Cl | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 4-C₆H₅ | —CH₂—CH₂— | cyclopropyl-CH₃ | N(CH) |
| 4-C₆H₄-Cl | " | " | " |
| 4-O-C₆H₅ | " | " | " |
| 4-O-C₆H₄-Cl | " | " | " |
| 4-CH₂-C₆H₅ | " | " | " |
| 4-CH₂-C₆H₄-Cl | " | " | " |

TABLE 1-continued
| $Z_m$ | Y | R | X |
|---|---|---|---|
| 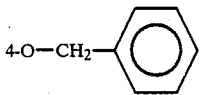 | " | " | " |
| 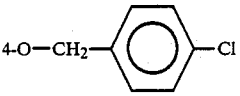 | " | " | " |
| 3,4-Cl$_2$ | " | " | " |
| 4-CF$_3$ | " | " | " |
| 4-OCF$_3$ | " | " | " |
| 4-SCF$_3$ | " | " | " |
| 4-SCH$_3$ | " | " | " |
| 4-C(CH$_3$)$_3$ | " | " | " |
| 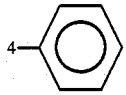 | —CH=CH— | —C(CH$_3$)$_3$ | N(CH) |
|  | " | " | ",* |
| 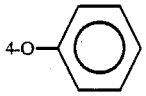 | " | " | " |
| 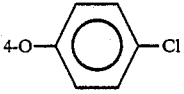 | " | " | " |
| 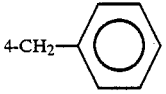 | " | " | " |
| 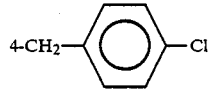 | " | " | " |
| 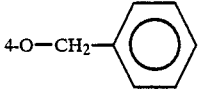 | " | " | " |
| 3,4-Cl$_2$ | " | " | " |
| 4-CF$_3$ | " | " | " |
| 4-OCF$_3$ | " | " | " |
| 4-SCF$_3$ | " | " | " |
| 4-SCH$_3$ | " | " | " |
| 4-C(CH$_3$)$_3$ | " | " | " |
| 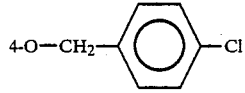 | —CH=CH— | 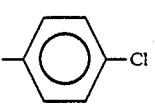 | N(CH) |

TABLE 1-continued

| $Z_m$ | Y | R | X |
|---|---|---|---|
| | " | " | " |
| 4-C₆H₄-Cl | | | |
| | " | " | " |
| 4-O-C₆H₅ | | | |
| | " | " | " |
| 4-O-C₆H₄-Cl | | | |
| | " | " | " |
| 4-CH₂-C₆H₅ | | | |
| | " | " | " |
| 4-CH₂-C₆H₄-Cl | | | |
| | " | " | " |
| 4-O-CH₂-C₆H₅ | | | |
| | " | " | " |
| 4-O-CH₂-C₆H₄-Cl | | | |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 4-C₆H₅ | —CH=CH— | —CH(CH₃)₂ | N(CH) |
| | " | " | " |
| 4-C₆H₄-Cl | | | |
| | " | " | " |
| 4-O-C₆H₅ | | | |
| | " | " | " |
| 4-O-C₆H₄-Cl | | | |
| | " | " | " |
| 4-CH₂-C₆H₅ | | | |

TABLE 1-continued
| $Z_m$ | Y | R | X |
|---|---|---|---|
| | " | " | " |
| 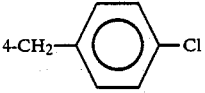 4-CH₂—◯—Cl | | | |
| 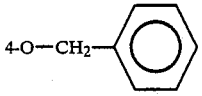 4-O—CH₂—◯ | " | " | " |
| 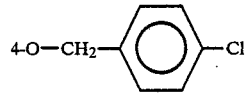 4-O—CH₂—◯—Cl | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 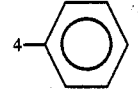 4-◯ | —CH=CH— |  H | N(CH) |
|  4-◯—Cl | " | " | " |
| 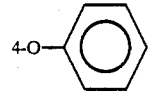 4-O-◯ | " | " | " |
| 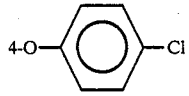 4-O—◯—Cl | " | " | " |
| 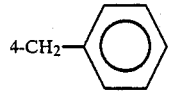 4-CH₂—◯ | " | " | " |
| 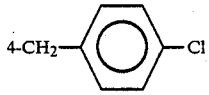 4-CH₂—◯—Cl | " | " | " |
| 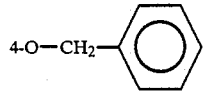 4-O—CH₂—◯ | " | " | " |
| 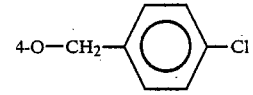 4-O—CH₂—◯—Cl | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |

TABLE 1-continued

| $Z_m$ | Y | R | X |
|---|---|---|---|
| 4-phenyl | —CH=CH— | cyclopropyl-CH₃ | N(CH) |
| 4-(4-Cl-phenyl) | " | " | " |
| 4-O-phenyl | " | " | " |
| 4-O-(4-Cl-phenyl) | " | " | " |
| 4-CH₂-phenyl | " | " | " |
| 4-CH₂-(4-Cl-phenyl) | " | " | " |
| 4-O-CH₂-phenyl | " | " | " |
| 4-O-CH₂-(4-Cl-phenyl) | " | " | " |
| 3,4-Cl₂ | " | " | " |
| 4-CF₃ | " | " | " |
| 4-OCF₃ | " | " | " |
| 4-SCF₃ | " | " | " |
| 4-SCH₃ | " | " | " |
| 4-C(CH₃)₃ | " | " | " |
| 4-Cl | —O—CH₂— | —CH(CH₃)₂ | N(CH) |
| 4-F | " | " | " |
| 4-CH₃ | " | " | " |
| 4-Cl | —O—CH₂— | cyclohexyl-H | N(CH) |
| 4-F | " | " | " |
| 4-CH₃ | " | " | " |
| 4-Cl | —O—CH₂— | cyclopropyl-CH₃ | N(CH) |
| 4-F | " | " | " |
| 4-CH₃ | " | " | " |
| 4-Cl | —CH₂—CH₂— | —CH(CH₃)₂ | N(CH) |
| 4-F | " | " | " |
| 4-CH₃ | " | " | " |

TABLE 1-continued

| $Z_m$ | Y | R | X |
|---|---|---|---|
| 4-Cl | —CH$_2$—CH$_2$— | ![cyclohexyl-H] | N(CH) |
| 4-F | " | " | " |
| 4-CH$_3$ | " | " | " |
| 4-Cl | —CH$_2$—CH$_2$— | ![cyclopropyl-CH$_3$] | N(CH) |
| 4-F | " | " | " |
| 4-CH$_3$ | " | " | " |
| 4-Cl | —CH=CH— | —CH(CH$_3$)$_2$ | N(CH) |
| 4-F | " | " | " |
| 4-CH$_3$ | " | " | " |
| 4-Cl | —CH=CH— | ![cyclohexyl-H] | N(CH) |
| 4-F | " | " | " |
| 4-CH$_3$ | " | " | " |
| 4-Cl | —CH=CH— | ![cyclopropyl-CH$_3$] | N(CH) |
| 4-F | " | " | " |
| 4-CH$_3$ | " | " | " |
| 2,4-Cl$_2$ | —CH$_2$—CH$_2$— | —C(CH$_3$)$_3$ | N(CH) |
| 4-CH$_3$ | " | " | " |
| 4-Cl, 2-CH$_3$ | " | " | " |
| 2,4-Cl$_2$ | —CH=CH— | —C(CH$_3$)$_3$ | N(CH) |
| 4-CH$_3$ | " | " | " |
| 4-Cl, 2-CH$_3$ | " | " | " |
| 4-F | —O—CH$_2$— | —C(CH$_3$)$_3$ | N(CH) |
| 2-CH$_3$ | —CH$_2$—CH$_2$— | —C(CH$_3$)$_3$ | N |
| 4-F | —CH=CH— | —C(CH$_3$)$_3$ | N |

If, for example, 2-(4-chlorophenoxy-methyl)-2tert.-butyl-oxirane and 1,2,4-triazole are used as starting substances, the course of the process for the preparation of compounds of the invention is illustrated by the following equation:

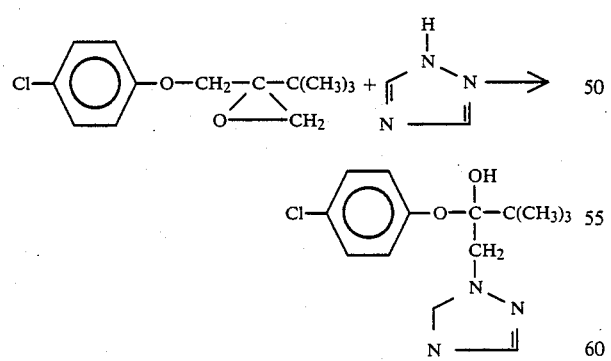

Preferred oxiranes of formula (II) to be used as starting substances for carrying out the process according to the invention are those in which R, Y, Z and m have those meanings which have already been mentioned in connection with the description of the preferred and particularly preferred compounds of the present invention.

The oxiranes of the formula

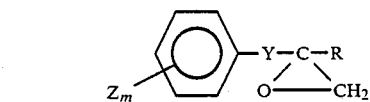

(II)

in which

R represents an alkyl radical, an optionally substituted cycloalkyl radical or an optionally substituted phenyl radical, Y represents a grouping —OCH$_2$—, —CH$_2$CH$_2$— or —CH=CH—, Z represents a halogen atom, an alkyl, cycloalkyl, alkoxy, alkylthio, halogenoalkyl, halogenoalkoxy or halogenoalkylthio radical, an optionally substituted phenyl radical, an optionally substituted phenoxy radical, an optionally substituted phenyl alkyl radical or an optionally substituted phenylalkoxy radical, m is 0, 1, 2 or 3, are novel.

The novel oxiranes of the formula (II) can be prepared by a process in which a ketone of the general formula

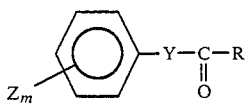

in which

R, Y, Z and m have the abovementioned meaning, is either (α) reacted with dimethyloxosulphonium methylide of the formula

in the presence of a diluent, or (β) reacted with trimethylsulphonium methyl-sulphate of the formula

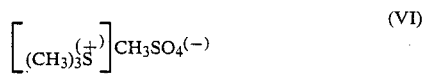

in the presence of an inert organic solvent and in the presence of a base.

The ketones of the formula (IV) required as starting substances in the preparation of the oxiranes of the formula (II) are known (see German Patent Specification 2,201,063, DE-OS (German Published Specification) 2,705,678, DE-OS (German Published Specification) 2,737,489, Tetrahedron 31, 3 (1975) and Chemical Abstracts 84, 73 906 n), or they can be prepared by processes which are known in principle.

The dimethyloxosulphonium methylide of the formula (V) required in process variant (α) is likewise known (see J. Amer. Chem. Soc. 87, 1363–1364 (1965)). It is processed in the above reaction in the freshly prepared state, by producing it in situ by reacting trimethyloxosulphonium iodide with sodium hydride or sodium amide in the presence of a diluent.

The trimethylsulphonium methyl-sulphate of the formula (VI) required in process variant (β) is likewise known (see Heterocycles 8, 397 (1977)). It is likewise employed in the above reaction in the freshly prepared state, by being produced in situ by reaction of dimethyl sulphide with dimethyl sulphate.

The preferred possible diluent in process variant (α) of the process of the preparation of the oxiranes of the formula (II) is dimethylsulphoxide.

The reaction temperatures can be varied within a substantial range in process variant (α) described above. In general, the reaction is carried out at a temperature between 20° C. and 80° C.

The process for the preparation of the oxiranes of the formula (II) by process variant (α) and the working up of the reaction mixture obtained in this synthesis are carried out by customary methods (see J. Amer. Chem. Sos. 87, 1363–1364 (1965)).

The preferred possible inert or organic solvent in process variant (β) for the preparation of the oxiranes of the formula (II) is acetonitrile.

Bases which can be used in process variant (β) are strong inorganic or organic bases. Sodium methylate is preferably used.

The reaction temperatures can be varied within a certain range in process variant (β) described above. In general, the reaction is carried out at a temperature between 0° C. and 60° C., preferably at room temperature.

The process for the preparation of the oxiranes of the formula (II) by process variant (β) and the working up of the reaction product obtained in this synthesis are carried out by customary methods (see Heterocycles 8, 397 (1977)).

The oxiranes of the formula (II) can, if appropriate, be further reacted directly in the process according to the invention without being isolated.

The azoles of the formula (III) are generally known compounds of organic chemistry.

Possible diluents for the reaction according to the invention for the production of 1-hydroxyethyl-azole derivatives of formula (I) are any of the inert organic solvents. These include, preferably, alcohols (such as ethanol and methoxyethanol), ketones (such as 2-butanone), nitriles (such as acetonitrile), esters (such as ethyl acetate), ethers (such as dioxane), aromatic hydrocarbons (such as benzene and toluene) and amides (such as dimethylformamide).

Possible bases for the reaction according to the invention are any of the inorganic and organic bases which can customarily be used. These include, preferably, alkali metal carbonates (such as sodium carbonate and potassium carbonate), alkali metal hydroxides (such as sodium hydroxide), alkali metal alcoholates (such as sodium methylate and ethylate and potassium methylate and ehtylate), alkali metal hydrides (such as sodium hydride), and lower tertiary alkylamines, cycloalkylamines and aralkylamines (such as, preferably, triethylamine).

The reaction temperatures can be varied within a substantial range in carrying out the process according to the invention. In general, the reaction is carried out at a temperature between 0° and 200° C., preferably between 60° and 150° C.

If appropriate, the reaction according to the invention can be carried out under increased pressure. The reaction is in general carried out under between 1 and 50 bars, preferably between 1 and 25 bars.

In carrying out the process according to the invention, 1 to 2 moles of azole and, if appropriate, 1 to 2 moles of base are preferably employed per mole of oxirane of the formula (II). The end products are isolated in the generally customary manner.

The compounds of the formula (I) obtainable by the process according to the invention can be converted into acid addition salts or metal salt complexes.

The following acids can preferably be used for the preparation of physiologically acceptable acid addition salts of the compounds of the formula (I): hydrogen halide acids (such as hydrobromic acid and, preferably hydrochloric acid, phosphoric acid, nitric acid, sulphuric acid, monofunctional and bifunctional carboxylic acids and hydroxycarboxylic acids (such as acetic acid, maleic acid, succinic acid, fumaric acid, tartaric acid, citric acid, salicyclic acid, sorbic acid and lactic acid) and sulphonic acids (such as p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII of the periodic system can preferably be used for the preparation of metal salt complexes of the compounds of the formula (I), examples of metals which may be mentioned being copper, zinc, manganese, magnesium, tin, iron and nickel.

Possible anions of the salts are, preferably, those which are derived from the following acids: hydrogen halide acids (such as hydrochloric acid and hydrobromic acid), phosphoric acid, nitric acid and sulphuric acid.

The metal complexes of compounds of the formula (I) can be obtained in a simple manner by customary processes, thus, for example, by dissolving the metal salt in alcohol, for example ethanol, and adding the solution to the compound of the formula (I). The metal salt complexes can be purified in a known manner, for example by filtration, isolation and, if appropriate, by recrystallisation.

The active compounds which can be used according to the invention engage in the metabolism of the plants and can therefore be employed as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

Plant growth regulating compounds can be employed, for example, to inhibit vegetative growth of the plants. Such inhibition of growth is inter alia of economic interest in the case of grasses, since it is thereby possible to reduce the frequency of cutting the grass in ornamental gardens, parks and sportsgrounds, at verges, at airports or in fruit orchards. The inhibition of growth of herbaceous and woody plants at verges and in the vicinity of pipelines or overland lines or, quite generally, in area in which heavy additional growth of plants is undesired, is also of importance.

The use of growth regulators to inhibit the growth in length of cereals is also important. The danger of lodging of the plants before harvesting is thereby reduced or completely eliminated. Furthermore, growth regulators can strengthen the stem of cereals, which again counteracts lodging. Use of growth regulators for shortening and strengthening the stem enables higher amounts of fertiliser to be applied to increase the yield, without danger of the cereal lodging.

In the case of many crop plants, inhibition of the vegetative growth makes denser planting possible, so that greater yields per area of ground can be achieved. An advantage of the smaller plants thus produced is also that the crop can be worked and harvested more easily.

Inhibition of the vegetative growth of plants can also lead to increases in yield, since the nutrients and assimilates benefit blossoming and fruit formation to a greater extent than they benefit the vegetative parts of plants.

Promotion of vegetative growth can also frequently be achieved with growth regulators. This is of great utility if it is the vegetative parts of the plants which are harvested. Promoting the vegetative growth can, however, also simultaneously lead to a promotion of generative growth, since more assimilates are formed, so that more fruit, or larger fruit, is obtained.

Increases in yield can in some cases be achieved by affecting the plant metabolism, without noticeable changes in vegetative growth. A change in the composition of plants, which in turn can lead to a better quality of the harvested products, can furthermore be achieved with growth regulators. Thus it is possible, for example, to increase the content of sugar in sugar beet, sugar cane, pineapples and citrus fruit or to increase the protein content in soya or cereals. Using the growth regulators it is also possible, for example, to inhibit the degradation of desired constituents, such as, for example, sugar in sugar beet or sugar cane, before or after harvesting. It is also possible favourably to influence the production or the efflux of secondary plant constituents. The stimulation of latex flux in rubber trees may be mentioned as an example.

Parthenocarpous fruit can be formed under the influence of growth regulators. Furthermore, the gender of the flowers can be influenced. Sterility of the pollen can also be produced, which is of great importance in the breeding and preparation of hybrid seed.

Branching of plants can be controlled by using growth regulators. On the other hand, by breaking the apical dominance the development of side shoots can be promoted, which can be very desirable, especially in the cultivation of ornamental plants, also in connection with growth inhibition. On the other hand, however, it is also possible to inhibit the growth of side shoots. There is great interest in this action, for example, in the cultivation of tobacco or in the planting of tomatoes.

The amount of leaf on plants can be controlled, under the influence of growth regulators, so that defoliation of the plants at a desired point in time is achieved. Such defoliation is of great importance in the mechanical harvesting of cotton, but is also of interest for facilitating harvesting in other crops, such as, for example, in viticulture. Defoliation of the plants can also be carried out to lower the transpiration of plants before they are transplanted.

The shedding of fruit can also be controlled with growth regulators. On the one hand, it is possible to prevent premature shedding of fruit. However, on the other hand, shedding of fruit, or even the fall of blossom, can be promoted up to a certain degree (thinning out) in order to interrupt the alternance. By alternance there is understood the peculiarity of some varieties of fruit to produce very different yields from year to year, for andogenic reasons. Finally, using growth regulators it is possible to reduce the force required to detach the fruit at harvest time so as to permit mechanical harvesting or facilitate manual harvesting.

Using growth regulators, it is furthermore possible to achieve an acceleration or retardation of ripening of the harvest product, before or after harvesting. This is of particular advantage, since it is thereby possible to achieve optimum adaptation to market requirements. Furthermore, growth regulators can in some cases improve the coloration of fruit. In addition, concentrating the ripening within a certain period of time is also achievable with the aid of growth regulators. This provides the preconditions for being able to carry out complete mechanical or manual harvesting in only a single pass, for example in the case of tobacco, tomatoes or coffee.

Using growth regulators, it is furthermore possible to influence the latent period of seeds or buds of plants, so that the plants, for example pineapple or ornamental plants in nurseries, germinate, shoot or blossom at a time at which they normally show no readiness to do so. Retarding the shooting of buds or the germination of seeds with the aid of growth regulators can be desirable in regions where frost is a hazard, in order to avoid damage by late frost.

Finally, the resistance of plants to frost, drought or a high salt content in the soil can be induced with growth regulators. Cultivation of plants in regions which are usually unsuitable for this purpose thereby becomes possible.

The preferred time of application of the growth regulators depends on the climatic and vegetative circumstances.

The foregoing description should not be taken as implying that each of the compounds can exhibit all of the described effects on plants. The effect exhibited by a compound in any particular set of circumstances must be determined empirically.

The active compounds according to the invention also exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chvtridiomvcetes, Zycomycetes, Ascomycetes, Basidiomycetes and Deuteromycetes.

The good toleration, by plants, of the active compounds, at the concentrations required for combating plant diseases, permits treatment of above-ground parts of plants, of vegative propagation stock and seeds, and of the soil.

As plant protection agents, the active compounds which can be used according to the invention can be particularly successfully employed for combating those fungi which cause powdery mildew diseases; thus, for combating Erysiphe species, such as, for example, against the powdery mildew of barley or of cereal causative organism (*Erysiphe graminis*).

It should be particularly emphasised that the active compounds according to the invention not only display a protective action but also have a systemic action. Thus, it is possible to protect plants from fungal attack when the active compound is fed to the above-ground parts of the plant via the soil and the root or via the seed.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations may be produced in known manner, for example by mixing the active compounds with extenders, that is to say liquid or liquefied gaseous or solid diluents or carriers, optionally with the use of surfaceactive agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts or iron, manganese, boron, copper, cobalt, molybdenum and zinc.

The formulations in general contain from 0.1 to 95 per cent by weight of active compound, preferably from 0.5 to 90 per cent by weight.

The active compounds according to the invention can be present in the formulations as a mixture with other known active compounds, such as fungicides, insecticides, acaricides and herbicides, and also as mixtures with fertilisers and other growth regulators.

The active compounds can be used as such, in the form of their formulations or as the use forms prepared therefrom, such as ready-to-use solutions, emulsifiable concentrates, emulsions, foams, suspensions, wettable powders, pastes, soluble powders, dusting agents and granules. They are used in the customary manner, for example by watering, spraying, atomising, scattering, dusting, foaming, coating and the like. Furthermore, it is possible to apply the active compounds in accordance with the ultra-low volume process or to inject the active compound preparation or the active compound itself into the soil. It is also possible to treat the seeds of plants.

When the compounds according to the invention are used as plant growth regulators, the amounts applied can be varied within a substantial range. In general, 0.01 to 50 kg, preferably 0.05 to 10 kg, of active compound are used per hectare of soil surface.

The amount applied can also be varied within a substantial range, depending on the type of application, when the substances according to the invention are used as fungicides. Thus, especially in the treatment of parts of plants, the active compound concentrations in the use forms are in general between 1 and 0.0001% by weight, preferably between 0.5 and 0.001%. In the treatment of seed, amounts of active compound of 0.001 to 50 g per kilogram of seed, preferably 0.01 to 10 g, are generally required. In the treatment of soil, active compound concentrations of 0.00001 to 0.1% by weight, preferably 0.0001 to 0.02%, are required at the place of action.

The present invention also provides plant growth regulation and fungicidal compositions containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention also provides a method of regulating the growth of plants which comprises applying to the plants, or to habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

The present invention further provides plants, the growth of which has been regulated by their being grown in areas in which immediately prior to and/or during the time of the growing a compound of the present invention was applied alone or in admixture with a diluent or carrier.

It will be seen that the usual methods of providing a harvested crop may be improved by the present invention.

Preparative Examples

EXAMPLE 1

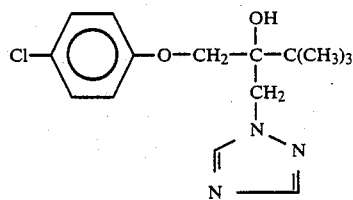

(I-1)

72.15 g (0.3 mole) of 2-(4-chlorophenoxy-methyl)-2-tert.-butyl-oxirane and 24.15 g (0.35 mole) of 1,2,4-triazole were heated under reflux in 120 ml of ethanol for 48 hours. The mixture was then concentrated, the residue was taken up in 200 ml of ethyl acetate and the ethyl acetate mixture was heated. It was then cooled in an ice bath and the solid was filtered off and rinsed with ethyl acetate. The filtrate was concentrated, the residue was dissolved in ether/hexane and the solution was gassed with hydrogen chloride. The precipitate was filtered off and rinsed with ether and the free base was obtained by adding ethyl acetate/1N sodium hydroxide solution. 60.2 g (65% of theory) of 2-(4-chlorophenoxy-methyl)-3,3-dimethyl-1-(1,2,4-triazole-1-yl)butan-2-ol of melting point 84°–87° C. were obtained.

Preparation of the starting material

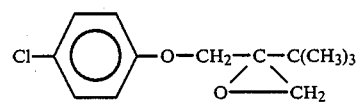

(II-1)

A solution of 162 ml (2.2 moles) of dimethyl sulphide in 400 ml of absolute acetonitrile was added to a solution of 189 ml (2.0 moles) of dimethyl sulphate in 1,200 ml of absolute acetonitrile at room temperature. The reaction mixture was stirred overnight at room temperature. 118.8 g (2.2 moles) of sodium methylate were then added. The mixture was stirred for 30 minutes and a solution of 272 g (1.2 moles) of 1-(4-chlorophenoxy)-3,3-dimethyl-butan-2-one in 600 ml of absolute acetonitrile was then added dropwise in the course of 30 minutes. The reaction mixture was subsequently stirred overnight. It was then concentrated, the residue was partitioned between water and ethyl acetate, the organic phase was separated off, washed twice with water and once with saturated sodium chloride solution, dried over sodium sulphate and concentrated and the residue was distilled in vacuo. 242.4 g (84% of theory) of 2-(4-chlorophenoxymethyl)-2-tert.-butyl-oxirane of boiling point 115°–22° C./0.003 mm Hg column and of melting point 50°–52° C. were obtained.

EXAMPLE 2

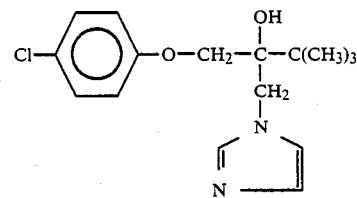

(I-2)

8.02 g (0.1178 mole) of imidazole were added to 2.71 g (0.1178 mole) of sodium in 250 ml of absolute ethanol. A solution of 14.17 g (0.0589 mole) of 2-(4-chlorophenoxy-methyl)-2-tert.-butyl-oxirane in 100 ml of ethanol was added dropwise at room temperature in the course of 30 minutes. The reaction was then heated under reflux for 8 hours and concentrated and the residue was taken up in ether. The ether mixture was extracted three times with 1N hydrochloric acid and the combined hydrochloric acid phases were neutralised with sodium bicarbonate and then extracted with ethyl acetate. After concentrating, and recrystallising the product from cyclohexane, 11.6 g (64% of theory) of 2-(4-chlorophenoxy-methyl)-3,3-dimethyl-1-(imidazol-1-yl)-butan-2 ol of melting point 154°–55° C. were obtained.

EXAMPLE 3

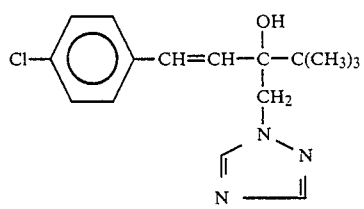

A solution of 17.75 g (0.075 mole) of 2-(4-chlorophenyl-ethenyl)-2-tert.-butyl-oxirane and 6.9 g (0.1 mole) of 1,2,4-triazole in 30 ml of ethanol was heated in a bomb tube at 150° C. for 20 hours. The reaction mixture was then concentrated and the crystalline residue was stirred with ether. The solid was then filtered off and recrystallised from acetonitrile. 17.7 g (77% of theory) of 1-(4-chlorophenyl)-4,4-dimethyl-3-(imidazol-1-yl-methyl)-1-penten-3-ol of melting point 139°–41° C. were obtained.

EXAMPLE 4

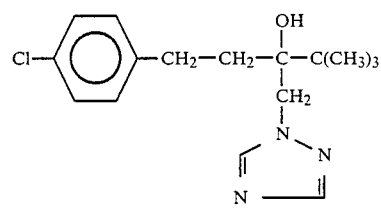

A solution of 17.9 g (0.075 mole) of 2-(4-chlorophenylethyl)-2-tert.-butyl-oxirane and 6.9 g (0.1 mole) of 1,2,4-triazole in 30 ml of ethanol was heated in a bomb tube at 150° C. for 20 hours. The reaction solution was allowed to cool and was concentrated. The residue was dissolved in ether and the solution was washed three times with water and once with sodium chloride solution, dried over sodium sulphate and concentrated. The residue was chromatographed over a silica gel column (mobile phase: methylene chloride/ethyl acetate 1:1). 12.3 g (53.2% of theory) of 1-(4-chlorophenyl)-4,4-dimethyl-3-(1,2,4-triazol-1-yl-methyl)-pentane-3-ol were obtained as a viscous oil.

The following compounds of the general formula (I) were obtained in an analogous manner:

TABLE 2

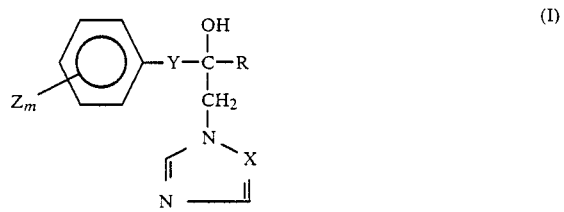

| Example No. | $Z_m$ | Y | R | X | Melting point (°C.) |
|---|---|---|---|---|---|
| I-5 | 4-Cl, 2-CH$_3$ | —O—CH$_2$— | —C(CH$_3$)$_3$ | N | 125,5–29 |
| 6 | 2,4-Cl$_2$ | —O—CH$_2$— | —C(CH$_3$)$_3$ | N | 120,5–25,5 |
| 7 | 4-CH$_3$ | —O—CH$_2$— | —C(CH$_3$)$_3$ | N | 98–101.5 |
| 8 | 2-CH$_3$ | —O—CH$_2$— | —C(CH$_3$)$_3$ | N | 89–101 |
| 9 | 4-F | —CH$_2$—CH$_2$— | —C(CH$_3$)$_3$ | N | 91–95,5 |
| 10 | 2-CH$_3$ | —CH=CH— | —C(CH$_3$)$_3$ | N | Oel |
| 11 | 4-Cl | —CH$_2$—CH$_2$— | —C(CH$_3$)$_3$ | N | 212(decomposition) (×HCl) |
| 12 | 2,4-Cl$_2$ | —O—CH$_2$— | —C(CH$_3$)$_3$ | CH | 152–54 |
| 13 | 4-CH$_3$ | —O—CH$_2$— | —C(CH$_3$)$_3$ | CH | 129–31 |
| 14 | 2-CH$_3$ | —O—CH$_2$— | —C(CH$_3$)$_3$ | CH | 123–24 |
| 15 | 4-Cl, 2-CH$_3$ | —O—CH$_2$— | —C(CH$_3$)$_3$ | CH | 157–59 |
| 16 | 4-Cl | —CH$_2$—CH$_2$— | —C(CH$_3$)$_3$ | CH | 157,5–59,5 |
| 17 | 4-F | —CH$_2$—CH$_2$— | —C(CH$_3$)$_3$ | CH | 124–25 |
| 18 | 2-CH$_3$ | —CH$_2$—CH$_2$— | —C(CH$_3$)$_3$ | CH | 94–99 |
| 19 | 4-Cl | —CH=CH— | —C(CH$_3$)$_3$ | CH | 158,5–62 |
| 20 | 4-F | —CH=CH— | —C(CH$_3$)$_3$ | CH | 144–46 |
| 21 | 2-CH$_3$ | —CH=CH— | —C(CH$_3$)$_3$ | CH | 127–32 |
| 22 | 4-Cl | —O—CH$_2$— |  | CH | 216–17 (×½ NDS)* |
| 23 | 4-CH$_3$ | —CH=CH— | —C(CH$_3$)$_3$ | N | 117–19 |
| 24 | 4-CH$_3$ | —CH=CH— | —C(CH$_3$)$_3$ | CH | 114–46 |
| 25 | 2,6-Cl$_2$ | —CH=CH— | —C(CH$_3$)$_3$ | CH | 110–16 |
| 26 | 4-CH$_3$ | —CH$_2$—CH$_2$— | —C(CH$_3$)$_3$ | N | Oil |
| 27 | 2,4-Cl$_2$ | —CH$_2$—CH$_2$— | —C(CH$_3$)$_3$ | CH | 118–19 |

TABLE 2-continued

Structure (I):
Ar(Zm)—Y—C(OH)(R)—CH2—N(—N=)(—X=) triazole/tetrazole with phenyl bearing Zm

| Example No. | Zm | Y | R | X | Melting point (°C.) |
|---|---|---|---|---|---|
| 28 | 4-phenyl | —O—CH2— | " | " | 169–70,5 |
| 29 | 2-Cl | —O—CH2— | " | " | 122–24 |
| 30 | 2-Cl | —O—CH2— | " | N | 109–11 |
| 31 | 2,4-Cl2 | —CH2—CH2— | " | " | 94–95 |
| 32 | 2-CH3 | —CH2—CH2— | " | " | 82–83 |
| 33 | 4-Cl | —O—CH2— | 2,4-Cl2-phenyl | CH | 134–35,5 |
| 34 | 4-phenyl | —O—CH2— | —C(CH3)3 | N | 118–19,5 |
| 35 | 4-Cl | —O—CH2— | 4-Cl-phenyl | " | 81–85 |
| 36 | 4-Cl | —O—CH2— | 2,4-Cl2-phenyl | " | 149–51 |
| 37 | 4-F | —O—CH2— | —C(CH3)3 | CH | 141–42 |
| 38 | 4-F | —O—CH2— | " | N | 73–75 |
| 39 | 3-Cl | —O—CH2— | " | CH | 124 |
| 40 | 2-Cl, 4-F | —O—CH2— | " | " | 137 |
| 41 | 3-Cl | —O—CH2— | " | N | 72 |
| 42 | 2-Cl, 4-F | —O—CH2— | " | " | 130 |
| 43 | 3,4-Cl2 | —O—CH2— | " | " | 124 |
| 44 | 4-CH3 | —CH2—CH2— | " | CH | 101–03 |
| 45 | 4-F | —CH=CH— | " | N | 129–31 |
| 46 | 4-Cl-phenyl | —O—CH2— | " | CH | 174–76 |
| 47 | 4-Cl-phenyl | —O—CH2— | " | N | 109–11 |
| 48 | — | —O—CH2— | —C(CH3)3 | N | 84–85 |
| 49 | 4-OCH3 | —O—CH2— | " | " | 63–66 |
| 50 | 4-C(CH3)3 | —O—CH2— | " | " | 75–78 |
| 51 | 4-OCF3 | —O—CH2— | " | " | $n_D^{20} = 1,4902$ |

$^H$NDS = 1,5-naphthalenedisulphonic acid

TABLE 3

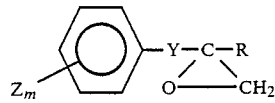
(II)

| Example No. | $Z_m$ | Y | R | Boiling point (°C.) mm Hg column |
|---|---|---|---|---|
| II-2 | 2,4-Cl$_2$ | —O—CH$_2$— | —C(CH$_3$)$_3$ | 125-27/0,3 |
| II-3 | 4-CH$_3$ | —O—CH$_2$— | " | 85/0,07 |
| II-4 | 2-CH$_3$ | —O—CH$_2$— | " | 89/0,07 |
| II-5 | 4-Cl,2-CH$_3$ | —O—CH$_2$— | " | 114-17/0,33 |
| II-6 | 4-Cl | —CH$_2$—CH$_2$— | " | 99-103/0,005 |
| II-7 | 2,4-Cl$_2$ | —CH$_2$—CH$_2$— | " | 79/0,004 |
| II-8 | 4-F | —CH$_2$—CH$_2$— | " | 79-89/0,003 |
| II-9 | 4-CH$_3$ | —CH$_2$—CH$_2$— | " | 74-78/0,003 |
| II-10 | 2-CH$_3$ | —CH$_2$—CH$_2$— | " | 95/0,005 |
| II-11 | 4-Cl | —CH=CH— | " | Melting point 61-62.5 |
| II-12 | 2,4-Cl$_2$ | —CH=CH— | " | not isolated |
| II-13 | 4-CH$_3$ | —CH=CH— | " | not isolated |
| II-14 | 4-F | —CH=CH— | " | 75/0,005 |
| II-15 | 2-CH$_3$ | —CH=CH— | " | 71-74/0,01 |
| II-16 | 2,6-Cl$_2$ | —CH=CH— | " | not isolated |

The plant growth regulant and fungicidal activity of the compounds of this invention is illustrated by the following biotest Examples.

In these Examples, the compounds according to the present invention are each identified by the number (given in brackets) of the corresponding preparative Example, which will be found earlier in this specification.

The known comparison compounds are identified as follows:

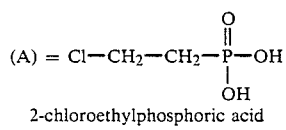

2-chloroethylphosphoric acid

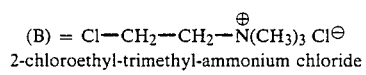

2-chloroethyl-trimethyl-ammonium chloride

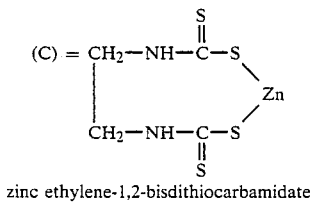

zinc ethylene-1,2-bisdithiocarbamidate

EXAMPLE A

Inhibition of growth of sugar beet

Solvent: 30 parts by weight of dimethylformamide
Emulsifier: 1 part by weight of polyoxyethylene sorbitane monolaurate To produce a suitable preparation of active compound, 1 part by weight of active compound was mixed with the stated amounts of solvent and emulsifier and the mixture was made up to the desired concentration with water.

Sugar beet was grown in a greenhouse until formation of the cotyledons was complete. In this stage, the plants were sprayed with the preparation of active compound until dripping wet. After 14 days, the additional growth of the plants was measured and the inhibition of growth in per cent of the additional growth of the control plants was calculated. 0% inhibition of growth denoted a growth which correspond to that of the control plants. 100% inhibition of growth meant that growth had stopped.

In this test, active compounds (I-1) and (I-7) exhibited a better inhibition of growth than the substance (B) known from the prior art.

EXAMPLE (B)

Inhibition of growth of soya beans

Solvent: 10 parts by weight of methanol
Emulsifier: 2 parts by weight of polyoxyethylene sorbitane monolaurate To produce a suitable preparation of active compound, 1 part by weight of active compound was mixed with the stated amounts of solvent and emulsifier and the mixture was made up to the desired concentration with water.

Young soya bean plants, in the stage in which the first secondary leaves had unfolded, were sprayed with the preparations of active compound until dripping wet. After 2 weeks, the additional growth was measured and the inhibition of growth in % of the additional growth of the control plants was calculated. 100% meant that growth had stopped and 0% denoted a growth corresponding to that of the untreated control plants.

In this test, active compounds (I-5) and (I-1) exhibited a better inhibition of growth than the substance (B) known from the prior art.

EXAMPLE C

Inhibition of growth of cotton

Solvent: 30 parts by weight of dimethyl formamide
Emulsifier: 1 part by weight of polyoxyethylene sorbitane monolaurate To produce a suitable preparation of active compound, 1 part by weight of active compound was mixed with the stated amounts of solvent and emulsifier and the mixture was made up to the desired concentration with water.

Cotton plants were grown in a greenhouse until the 5th secondary leaf had unfolded completely. In this stage, the plants were sprayed with the preparations of active compound until dripping wet. After 3 weeks, the additional growth or the plants was measured and the inhibition of growth in per cent of the additional growth of the control plants was calculated. 100% inhibition of growth meant that growth had stopped and 0% denoted a growth corresponding to that of the control plants.

In this test, active compounds (I-1) and (I-7) exhibited a better inhibition of growth than the substance (A) known from the prior art.

EXAMPLE D

Stimulation of the assimilation of $CO_3$ in soya beans

Soya beans were treated with the preparations of active compound as described in biotest Example (B). 7 days after the treatment, the assimilation of $CO_2$ was measured on discs of leaf from these plants and corresponding control plants with the aid of an infra-red gas analyser. Active compounds (5), (9), (18) and (28) exhibited, in concentrations of 250, 500 and 1,000 ppm, a considerably increased assimilation of $CO_2$ compared with the controls. From this effect, increases in yield as a result of the active compound could have been expected.

EXAMPLE E

Erysiphe test (barley/protective/

Solvent: 100 parts by weight of dimethylformamide
Emulsifier: 0.25 part by weight of alkylaryl polyglycol ether To produce a suitable preparation of active compound, 1 part by weight of active compound was mixed with the stated amounts of solvent and emulsifier, and the concentrate was diluted with water to the desired concentration.

To test for protective activity, young plants were sprayed with the preparation of active compound until dew-moist. After the spray coating had dried on, the plants were dusted with spores of *Erysiphe graminis* f.sp. *hordei*.

The plants were placed in a greenhouse at a temperature of about 20° C. and a relative atmospheric humidity of about 80%, in order to promote the development of powdery mildew pustules.

Evaluation was carried out 7 days after the inoculation.

In this test, a significantly superior activity compared with the substance (C) known from the prior art was shown, for example, by the compounds (I-5) (I-6) (I-1) (I-7) (I-8) (I-9) (I-2) (I-12) (I-13) and (I-15).

EXAMPLE F

Powdery mildew of barley test (*Erysiphe graminis* var. *hordei*)/systemic (fungal disease of cereal shoots)

The active compounds were used as pulverulent seed treatment agents. These were produced by extending the active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favourable conditions in a greenhouse. 7 days after sowing, when the barley plants had unfolded their first leaf, they were dusted with fresh spores of *Erysiphe graminis* var. *hordei* and grown on at 21°-22° C. and 80-90% relative atmospheric humidity and 16 hours' exposure to light. The typical mildew pustules formed on the leaves within 6 days.

The degree of infection was expressed as a percentage of the infection of the untreated control plants. Thus, 0% denoted no infection and 100% denoted the same degree of infection as in the case of the untreated control. The more active was the active compound, the lower was the degree of mildew infection.

In this test, a significantly superior activity compared with the substance (C) known from the prior art is shown, for example, by the compound (I-9).

It will be understood that the specification and examples are illustrative, but not limitative of the present invention and that other embodiments within the spirit and scope of the invention will suggest themselves to those skilled in the art.

What is claimed is:

1. A 1-hydroxyethyl-azole of the formula

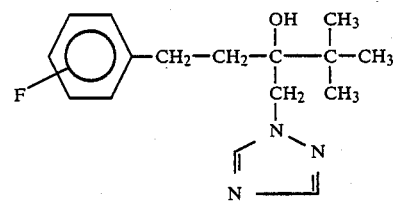

or an acid addition salt or metal salt complex thereof.

2. A compound according to claim 1, wherein such compound is 1-(4-fluorophenyl)-4,4-dimethyl-3-(1,2,4-triazol-1-yl-methyl)-pentan-3-ol of the formula

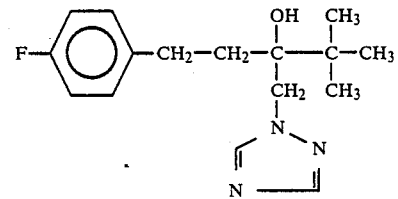

or an acid addition salt or metal salt complex thereof.

3. A plant growth regulant composition containing, as an active ingredient, an effective amount of a compound as claimed in claim 1 in admixture with an inert solid or liquefied gaseous diluent or carrier.

4. A method of regulating plant growth which comprises applying to the plants or to a habitat thereof an effective amount of a 1-hydroxyethyl-azole compound as claimed in claim 1 alone or in admixture with an inert diluent or carrier.

5. The method according to claim 4, wherein the compound is 1-(4-fluorophenyl)-4,4-dimethyl-3-(1,2,4-triazol-1-yl-methyl)-pentan-3-ol or an acid addition salt or metal salt complex thereof.

6. A fungicidal composition containing, as an active ingredient, an effective amount of a compound as claimed in claim 1 in admixture with an inert solid or liquefied gaseous diluent or carrier.

7. A method of combating fungi which comprises applying to the fungi or to a habitat thereof an effective amount of a 1-hydroxyethyl-azole compound as claimed in claim 1 alone or in admixture with an inert diluent or carrier.

8. The method according to claim 7, wherein the compound is 1-(4-fluorophenyl)-4,4-dimethyl-3-(1,2,4-triazol-1-yl-methyl)-pentan-3-ol or an acid addition salt or metal salt complex thereof.

* * * * *